US008688192B2

(12) United States Patent
Wu et al.

(10) Patent No.: US 8,688,192 B2
(45) Date of Patent: Apr. 1, 2014

(54) HIGH-RESOLUTION MAGNETOCARDIOGRAM RESTORATION FOR CARDIAC ELECTRIC CURRENT LOCALIZATION

(75) Inventors: Chenyu Wu, Mountian View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 449 days.

(21) Appl. No.: 13/017,869

(22) Filed: Jan. 31, 2011

(65) Prior Publication Data

US 2012/0197145 A1    Aug. 2, 2012

(51) Int. Cl.
*A61B 5/04*    (2006.01)
(52) U.S. Cl.
USPC ............................ 600/409; 600/407; 382/128
(58) Field of Classification Search
USPC ................................................. 600/407–480
See application file for complete search history.

(56) References Cited

U.S. PATENT DOCUMENTS

| 2006/0122486 A1* | 6/2006 | Tamez-Pena et al. | 600/410 |
| 2010/0137727 A1* | 6/2010 | Sameni et al. | 600/511 |
| 2011/0313274 A1* | 12/2011 | Subbarao | 600/409 |

OTHER PUBLICATIONS

Erne, S. N., et al., "Magnetocardiography under Clinical Conditions", Biomedizinische Technik, vol. 44, No. s2, Jan. 1999.
Arturi, C. M., et al., "Information Content in Single-Component Versus Three-Component Cardiomagnetic Fields", IEEE Transactions on Magnetics, vol. 40, No. 2 Mar. 2004.
Jiang, S., et al., "Dipole Source Localization in Magnetocardiography", Proceedings of NFSI & ICFBI, Oct. 2007.
Fenici, R., et al., "Phantom Validation of Multichannel Magnetocardiography Source Localization", Pacing and Clinical Electrophysiology, vol. 26: pp. 426-430, 2003.
Agren, P.L., et al., "Magnetocardiographic Localization of Arrhythmia Substrates: A Methodology Study with Accessory Pathway Ablation as Reference", IEEE Trans. on Medical Imaging, vol. 17, No. 3, Jun. 1998.
Jiang, S., et al., "ANN Interpolation in MCG Mapping", Proceedings of the 2005 IEEE, Engineering in Medicine and Biology, 27th Annual Conference Sep. 1-4, 2005.
Nomura, M., et al., "Evaluatiion of an Infarction Vector by Magnetocardiogram: Detection of Electromotive Forces that cannot be Deduced from an Electrocardiogram", International Congress Series 1300, pp. 512-515, 2007.
Stroink, G., "Forty Years of Magnetocardiology", BIOMAG2010, IFMBE Proceedings 28, pp. 1-8, 2010.

(Continued)

*Primary Examiner* — Tse Chen
*Assistant Examiner* — Vani Gupta

(57) ABSTRACT

Magnetocardiogram (MCG) provides temporal and spatial measurements of cardiac electric activities, which permits current localization. An MCG device usually consists of a small number of magnetic sensors in a planar array. Each sensor provides a highly low-resolution 2D MCG map. Such a low-res map is insufficient for cardiac electric current localization. To create a high resolution MCG image from the sparse measurements, an algorithm based on model learning is used. The model is constructed using a large number of randomly generated high resolution MCG images based on the Biot-Savart Law. By fitting the model with the sparse measurements, high resolution MCG image are created. Next, the 2D position of the electric current is localized by finding the peak in the tangential components of the high resolution MCG images. Finally, the 2D current localization is refined by a non-linear optimization algorithm, which simultaneously recovers the depth of the electric current from the sensor and its magnitude and orientation.

18 Claims, 14 Drawing Sheets

(56) References Cited

OTHER PUBLICATIONS

Tsukada, K., et al., "Newly Developed Magnetocardiographic System for Diagnosing Heart Disease", Hitachi Review, vol. 50, No. 1, pp. 13-17, 2001.

Weismuller, P., et al., "Magnetocardiographic Non-Invasive Localization of Accessory Pathways in the Wolff-Parkinson-White syndrome by a Multichannel System", European Heart Journal, 13, pp. 616-622, 1992.

Yamada, S., et al., "Noninvasive Diagnosis of Arrhythmic Foci by Using Magnetocardiograms Method and Accuracy of Magneto-Anatomical Mapping System", Journal of Arrhythmia, vol. 16, No. 5, pp. 580-586, 2000.

Yamada, S., et al., Magnetocardiograms in Clinical Medicine: Unique Information on Cardiac Ischemia, Arrhythmias, and Fetal Diagnosis, Internal Medicine, vol. 44, No. 1, Jan. 2005.

* cited by examiner $$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M \qquad Eq.\ 1$$

$$B_z(\vec{r_m}) = \frac{\mu_0}{4\pi} \frac{[-J^2, J^1] \cdot [r_m^1 - x_p, r_m^2 - y_p]'}{[(r_m^1 - x_p)^2 + (r_m^2 - y_p)^2 + (r_m^3 - z_p)^2]^{3/2}} \qquad Eq.\ 2$$

$$B_z(m) = \frac{a_m}{[b_m + (c-z)^2]^{3/2}} \qquad Eq.\ 3$$

$$\begin{aligned} B_z^m(z + \Delta z) \\ = B_z^m(z) + \frac{d}{dz} B_z^m(z) \cdot \Delta z + \frac{d^2}{2dz} B_z^m(z) \cdot \Delta z^2 + O(\Delta z^3) \end{aligned} \qquad Eq.\ 4$$

$$B_{xy}(i,j) = \sqrt{(\partial B_z(i,j)/\partial x)^2 + (\partial B_z(i,j)/\partial y)^2} \qquad Eq.\ 5$$

$$\vec{B^m} = \vec{J} \times \vec{R_m} = -\vec{R_m} \times \vec{J} \qquad Eq.\ 6$$

where $\vec{B^m} = \vec{B}(\vec{r_m})$, $\vec{J} = \vec{J}(\vec{p})$ and $\vec{R_m} = \frac{\mu_0}{4\pi} \frac{(\vec{r_m} - \vec{p})}{\|\vec{r_m} - \vec{p}\|^3}$

FIG. 12A $$\vec{B^m} = -[\vec{R_m}]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \quad Eq.\ 7$$

$$B_z^m = \begin{bmatrix} R_m^2, & -R_m^1 \end{bmatrix} \cdot \begin{bmatrix} J^1, J^2 \end{bmatrix}' \quad Eq.\ 8$$

$$\underbrace{\begin{bmatrix} B_z^1 \\ B_z^2 \\ \vdots \\ B_z^M \end{bmatrix}}_{\mathbf{B}} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{\mathbf{R}} \cdot \underbrace{\begin{bmatrix} J^1 \\ J^2 \end{bmatrix}}_{\mathbf{J}} \quad Eq.\ 9$$

$$\mathbf{J} = (\mathbf{R}^T \mathbf{R})^{-1} \mathbf{R}^T \mathbf{B} \quad Eq.\ 10$$

$$\vec{B^m} = \frac{\mu_0}{4\pi} \frac{\vec{J} \times ((\vec{r_0} + \vec{\delta_m}) - \vec{p})}{\|(\vec{r_0} + \vec{\delta_m}) - \vec{p}\|^3} = \frac{\mu_0}{4\pi} \frac{\vec{J} \times (\vec{\epsilon_0} + \vec{\delta_m})}{\|\vec{\epsilon_0} + \vec{\delta_m}\|^3} \quad Eq.\ 11$$

FIG. 12B $$\alpha \vec{B}^m = \frac{\vec{J} \times \vec{\epsilon_0} + \vec{J} \times \vec{\delta_m}}{\|\vec{\epsilon_0} + \vec{\delta_m}\|^3} \qquad Eq.\ 12$$

$$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}}$$
$$= f^m(x_\epsilon, y_\epsilon, z_\epsilon) = 0 \qquad Eq.\ 13$$

$$z = d/\sqrt{2}, \|\vec{J}\| = \frac{4\pi d^2 B_z^{max}}{0.385 \mu_0} \qquad Eq.\ 14$$

FIG. 12C

Table 1. 2D Current Localization Error $\sqrt{(x_p - x_g)^2 + (y_p - y_g)^2}$

| Noise | 5% | 10% | 15% |
|---|---|---|---|
| Gaussian Distribution $G(0,1)$ | 0.99 +/- 0.81 mm | 2.02 +/- 1.85 mm | 3.37 +/- 2.83 mm |
| Uniform Distribution $(0,1)$ | 1.24 +/- 1.17 mm | 2.31 +/- 2.21 mm | 3.65 +/- 3.53 mm |

FIG. 13a

Table 2. 3D Current Localization Error $\sqrt{(x_p - x_g)^2 + (y_p - y_g)^2 + (z_p - z_g)^2}$

| Noise | 5% | 10% | 15% |
|---|---|---|---|
| Gaussian Distribution $G(0,1)$ | 1.68 +/- 1.36 mm | 3.30 +/- 2.60 mm | 5.02 +/- 3.97 mm |
| Uniform Distribution $(0,1)$ | 2.49 +/- 2.34 mm | 5.15 +/- 4.56 mm | 7.38 +/- 8.83 mm |

FIG. 13b

Table 3. Current Moment Reconstruction Error: Magnitude $\frac{\|\vec{\tau}_{rec}\| - \|\vec{\tau}_g\|}{\|\vec{\tau}_g\|}$

| Noise | 5% | 10% | 15% |
|---|---|---|---|
| Gaussian Distribution $G(0,1)$ | 2.2% +/- 1.8% | 4.7% +/- 4.6% | 6.0% +/- 5.7% |
| Uniform Distribution $(0,1)$ | 3.0% +/- 3.0% | 4.7% +/- 5.0% | 8.0% +/- 8.2% |

FIG. 13c

Table 4. Current Moment Reconstruction Error: Orientation $|atan2(x_p, y_p) - atan2(x_g, y_g)|$

| Noise | 5% | 10% | 15% |
|---|---|---|---|
| Gaussian Distribution $G(0,1)$ | 0.20° +/- 0.27° | 0.46° +/- 0.58° | 0.64° +/- 0.73° |
| Uniform Distribution $(0,1)$ | 0.30° +/- 0.32° | 0.77° +/- 0.95° | 1.02° +/- 1.12° |

FIG. 13d

HIGH-RESOLUTION MAGNETOCARDIOGRAM RESTORATION FOR CARDIAC ELECTRIC CURRENT LOCALIZATION

BACKGROUND

1. Field of Invention

The present invention relates the field of magnetocardiogram (MCG) imaging. More specifically, it relates to the generation of high-resolution MCG images from sparse data input from an electromagnetic sensor unit.

2. Description of Related Art

Cardiac electric currents are generated by electrophysiological processes in the heart. Localizing abnormal electric currents is very important for diagnosing ischemic diseases such as myocardial infarction, angina cordis, etc. It also benefits patients in the catheter lab for both treatment and follow-up, as is explained in "Forty Years of Magnetocardiology", by F. Stroink, in Int. Conf. on Biomagnetism Advances in Biomagnetism, 28:1-8, 2010.

Traditionally, cardiac electric activities such as arrhythmia are diagnosed by means of an electrocardiogram (ECG). However, since an ECG only provides temporal information, it cannot localize abnormal currents in the heart directly, even if the ischemic disease has been detected. However, by using a large number of electrodes (leads), Body Surface Potential Mapping (BSPM) is able to reconstruct a body surface potential map, as is explained in "Noninvasive volumetric imaging of cardiac electrophysiology", by Wang et al., in *CVPR*, pages 2176-2183, 2009. Nonetheless, the accuracy of electric current localization is still limited because the signals are often distorted due to the poor conductivity of body tissue.

The advent of the magnetocardiogram, or magnetocardiography, (MCG) provides more accurate measurements of cardiac electric currents, both spatially and temporally. With reference to FIG. 1A, an MCG system consists of a sensor unit 11 consisting of a small number of electromagnetic sensors 13 (typically arranged as a planar array of sixty-four or fewer sensors). Electrical impulses within the body create a magnetic field 15. In the present case, the human heart 19 functions as the observed current source 17.

Each sensor 13 is a capture point, and hereinafter may be referenced as a capture 13. Each capture 13 measures a one-dimensional (i.e. 1D) magnetic waveform in a direction perpendicular to the sensor planar array (i.e. the z-direction) emanating from the patient's chest 21 (i.e. human torso). The MCG sensor unit 11 is usually placed five to ten centimeters above the patient's chest 21, and measures the patient's heart magnetic field in a non-invasive way. At each capture 13 a low resolution (hereinafter, low-res), two-dimensional (2D) MCG map of electromagnetic activity is measured.

Compared to ECG, MCG has a few advantages. First, the magnetic field generated by the heart's electrical impulses (i.e. currents) is not distorted in the direction perpendicular to the body surface (i.e., z direction), due to the magnetic property of body tissue. Thus MCG is more accurate and sensitive to weak electrical activities in the early stage of heart disorders. Second, the MCG sensor array can localize the position of electrical currents in the heart. Finally, MCG measurements are non-invasive. After forty years of research in MCG, cardiac electric current localization and high resolution visualization for MCG measurements are attracting more and more interest from both research and clinical areas.

However, there are a number of difficulties associated with MCG, which so far has prevented MCG from becoming a mainstream medical diagnostic tool in cardiology. One difficulty is that the low-res 2D MCG maps are not sufficient for localizing electric currents in the heart. For example, a 64 channel Hitachi™ MCG system with a 25 mm sensor interval (as described in "Newly Developed Magnetocardiographic System for Diagnosing Heart Disease", by Tsukada et al., in *Hitachi Review*, 50(1):13-17, 2001) only measures an 8×8 MCG map (i.e. an 8×8 array of 64 measurement points).

The resolution of an MCG map is limited due to the size of the sensors 13, which limit the number of sensors 13 that an MCG sensor unit 11 may have.

Thus, a necessary step in MCG, is creating a high resolution (hereinafter High-res) MCG image, or map, from a low-res 2D MCG map. Two image examples 23 and 25 of such high-res images are shown in FIG. 1B. Image 23 shows the tangential image of a restored high-res MCG image of a healthy heart. The maximal point 25 (i.e. strongest point) within image 23 indicates the location (or source) of electric current in the heart. Thus, high-res MCG images permits doctors to directly "see" the electrical activity in the heart. Image 25 shows the tangential image of a restored high-res MCG image of an unhealthy heart. It differs significantly from image 23 of a healthy heart, and thus provides important cues for diagnosis. Compared to low-res MCG maps, high-res MCG images provide more diagnostic significance, and serve as the basis for an accurate electric current localization.

Most current MCG systems use curve fitting interpolation methods to reconstruct high-res MCG images from low-res 2D MCG maps, as is shown in "Magnetocardiographic Localization of Arrhythmia Substrates: A Methodology Study With Accessory Path-Way Ablation as Reference", by B. A. S. et al., in *Ann Noninvasive Electrocardiol*, 10(2):152-160, 2005, and shown in "Evaluation of an Infarction Vector by Magnetocardiogram: Detection of Electromotive Forces that Cannot be Deduced from an Electrocardiogram", by Nomura et al, in *Int. Congress Series*, 1300:512-515, 2007. Unfortunately, the accuracy of curve fitting methods is usually limited.

Another method for improving the accuracy of high-res MCG images first reconstructs a three-dimensional (3D) position, magnitude and orientation of electric currents, given the low-res MCG measurements. This method is generally called the inverse problem, and is more fully explained in "Magnetocardiographic Localization of Arrhythmia Substrates: A Methodology Study with Accessory Pathway Ablation as Reference", by R. J. et al., in *Europace*, 11(2):169-177, 2009, and explained in "Conversion of Magnetocardiographic Recordings Between Two Different Multichannel Squid Devices", by M. B. et al., in *IEEE Trans. on Biomedical Engineering*, 47(7):869-875, 2000. This method generally computes a high-res MCG image based on current reconstructed by the Biot-Savart law.

As it is known in the art, however, according to the Helmboltz reciprocity principal, the inverse problem for MCG is an ill posed problem unless the number of electric currents is known. But even when the current number is known, it requires solving a large scale nonlinear optimization problem which is often computationally expensive and may lead to undesired local minimum.

R. J. et al. therefore propose a simplified solution by assuming a single electric current located at the world origin and far from the sensor array. As it is known in the art, linear solutions may be presented for special cases where the current positions are fixed at uniform grids in the heart. The presented linear solutions can be over-constrained or under-constrained. These methods, however, make another assumption that the sensor array and heart are perfectly aligned. In practice, these assumptions often can be difficult to satisfy.

Therefore, high-res MCG image restoration based on these types of methods can often be unreliable.

Recently machine learning techniques have been applied to high-res MCG image restoration. An example of this approach applies learned nonlinear interpolation functions using neural networks.

SUMMARY OF INVENTION

An object of the present invention is a method of creating more accurate high-res MCG images.

Another object of the present invention is to provide a less computing-intensive approached toward generating accurate high-res MCG images form low-res 2D maps.

A further object of the present invention is to eliminate the need for assumption regarding the alignment of an MCG system and a patient's torso.

These objects are achieved by considering the high-res MCG image restoration as an example based super-resolution problem. Typically, one would require a library of true examples from which to learn characteristic of such true examples. However, since it is infeasible to measure dense magnetic fields, and thus not feasible to obtain such true example from direct measures, the presently preferred embodiment uses a model learning algorithm based on synthetic high-res MCG images. The sample images are randomly generated based on the Biot-Savart Law. From these samples the algorithm constructs a linear model by principal component analysis (PCA). By projecting the sparse measurements into the subspace of the linear model, the model coefficients are estimated and the high-res MCG image can be restored as a model instance.

As is explained above, an MCG image typically provides low-res, 2D MCG maps, and the inverse problem (i.e. reconstruction of the position and moment of the electric current) would typically be applied to the low-res, 2D MCG maps. It is presently preferred, however, that the inverse problem be applied to the restored high-res MCG image.

Given the high-res MCG image, the 2D position of the electric current can be localized as the maximal point of the tangential components of the high-res MCG image. To improve the 2D localization accuracy, a nonlinear optimization algorithm is developed to solve the inverse problem. At the same time, the depth, magnitude and orientation of the electric current are also recovered. More specifically, the preferred algorithm alternates two steps iteratively. The first step estimates the 3D current position, and the second step reconstructs its magnitude and orientation. The 2D current location estimated from the model based restoration is used as the initialization. The present method is efficient, accurate and reliable without the need of special assumptions.

The above objects are met in a magnetocardiogram (MCG) system comprising: a sensor unit including M×M electromagnetic sensors producing a sparse measurement output of M×M data units, said sparse measurement output constituting a first MCG image; a linear model defining a second MCG image of substantially higher resolution than said first MCG image, said second MCG image having a P×P resolution where P>M, said linear model establishing interpolation patterns between characteristics of the linear model and any data point of said M×M measurement output; and a high resolution MCG image synthesizer for producing a third MCG image by projecting said first MCG image onto the subspace of the linear model, and establishing coefficients for said third MCG image in accordance with the linear model and said M×M data units.

In this MCG system, the third MCG image has a P×P resolution.

Preferably, the MCG system further has an electric current localizer for determining a position and momentum of an electric current in accord with said third MCG image, said electric current localizer evaluating the electromagnetic output data from each electromagnetic sensor in an x-y orientation (Bxy) assuming single dipole, computing dense Bxy from dense Bz, finding the image maximum in said third MCG image, and using this determined position information as a starting point in an iterative process for identifying a three-dimensional position vector $\vec{p}$ and momentum vector $\vec{J}$ for said electric current.

In this approach, the identifying a three-dimensional position vector $\vec{p}$ and momentum vector $\vec{J}$ for said electric current further includes: Given said third MCG image $B_z(i,j)(i=1, 2, \ldots, N; j=1, 2, \ldots, N)$, the maximal point of the tangential components $B'_{xy}(i,j)$ of $B_z(i,j)$ refers to the 2D position $(x_p, y_p)$ of the electric current, and the tangential components of $B_z(i,j)$ is computed as $B_{xy}(i,j)=\sqrt{(\partial B_z(i,j)/\partial x)^2+(\partial B_z(i,j)/\partial y)^2}$; and said iterative process for identifying position vector $\vec{p}$ and momentum vector $\vec{J}$ for said electric current includes: (a) defining the Biot-Sarvart Law as $\vec{B}^m = \vec{J} \times \vec{R}_m = -\vec{R}_m \times \vec{J}$, where $\vec{B}^m = \vec{B}(\vec{r}_m)$, $\vec{J}=\vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Sarvart Law to a matrix form by using a skew-symmetric matrix:

$$\vec{B}^m = -[\vec{R}_m]_\times \vec{J}$$

$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]'$$

where $R_m^1, R_m^2$ are x,y components of $\vec{R}_m$, and for said M×M electromagnetic sensors one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimation of J defined as $J=(R^T R)^{-1} R^T B$; (c) defining the Biot-Sarvart Law $$\vec{B}^m = \frac{\mu_o}{4\pi} \frac{\vec{J} \times ((\vec{r}_o + \vec{\delta}_m) - \vec{p})}{\|(\vec{r}_o + \vec{\delta}_m) - \vec{p}\|^3} = \frac{\mu_o}{4\pi} \frac{\vec{J} \times (\vec{\varepsilon}_o + \vec{\delta}_m)}{\|\vec{\varepsilon}_o + \vec{\delta}_m\|^3},$$

letting $\alpha = 4\pi/\mu_0$ and $\vec{\varepsilon}_o = \vec{r}_o - \vec{p}$, identifying $\vec{\delta}_m$ as known for each sensor to redefining the Biot-Sarvart Law as $$\alpha \vec{B}^m = \frac{\vec{J} \times \vec{\varepsilon}_o + \vec{J} \times \vec{\delta}_m}{\|\vec{\varepsilon}_o + \vec{\delta}_m\|^3}$$

letting $\vec{\tau}_m = \vec{J} \times \vec{\delta}_m$ and $\vec{\varepsilon} = (x_\varepsilon, y_\varepsilon, z_\varepsilon)^T$ and computing $\vec{\tau}_m$ from $\vec{J}$, for each sensor m=1:M, defining a nonlinear equation in terms of $(x_\varepsilon, y_\varepsilon, z_\varepsilon)$ as $$\alpha B_z^m + \frac{-J_{x_\varepsilon}^2 + J_{y_\varepsilon}^1 + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F=(f^1; f^2; \ldots; f^M)=0$, and solving a least square solution of the nonlinear system F for $\vec{\varepsilon}_o$; (d) using $\vec{\varepsilon}_o$ from step (c) to update the position matrix R and recompute J as in step (b), and iteratively repeat steps steps (b) and (c) until converges is achieved; and (e) defining the $\vec{p} = \vec{r}_o - \vec{\varepsilon}_o$, and defining the initial depth z and magnitude $\|\vec{J}\|$ of the electric current as $$z = d/\sqrt{2} \cdot .3 \text{ cm}, \|\vec{J}\| = \frac{4\pi d^2 B_z^{max}}{0.385 \, \mu_0}$$

where d is the distance between two magnetic poles in the third MCG image.

Further preferably, in the present MCG system, the linear model is defined as creating a plurality of synthesized magnetocardiogram images having the same resolution as said second MCG image, said synthesized magnetocardiogram images being based on simulated electrical impulses within a three-dimensional spatial heart volume, as it would be perceived in an expected magnetocardiogram system.

In this case, the plurality of synthesized magnetocardiogram images includes at least one thousand synthesized images simulating perceived electrical impulses per predefined depth level within said heart volume.

Additionally, the synthesized MCG images are synthesized using the Biot-Savart Law.

Also, the synthesized MCG images are based on randomly generated currents within said heart volume.

Furthermore, the linear model is created using by principal component analysis (PCA).

In the presently preferred MCG system, the interpolation patterns are established by the following steps: (A) defining the following notation: N×N dense Bz magnetic field map to form a vector; M×M sparse measurement to form a vector; K randomly generated single current dipoles Q; (B) for each randomly generated current Q, compute N×N magnetic field map using Biot-Savart equation and stack the image to a vector $f_1$; (C) repeating step (B) to obtain K samples and get a data matrix $A=[f_1, f_2, \ldots f_K]$; and (D) training a PCA model given input data A, to obtain the eigenmatrix $\Sigma_f$.

In an embodiment of the present invention, the third MCG image is created by: given a new dipole and M×M sparse measurements $g_j$ finding the corresponding rows in the eigenmatrix, and denoting a resultant submatrix as $\Sigma_g$; projecting the sparse measurement to the PCA subspace and computing the coefficients as $c_g = \Sigma_g^+(g_j - g_{mean})$, where $\Sigma_g^+$ is an estimation of the inverse of $\Sigma_g$; and using the computed coefficients and original PCA space to reconstruct the dense magnetic field map Bz, as $f_j = \Sigma_f c_g + f_{mean}$.

Also in an embodiment of the present invention, the producing of said third MCG image includes: defining the sparse measurement output as a vector g; defining the linear model as $\Sigma$; extracting from $\Sigma$ the row corresponding to sparse measurement output to form a sub-eigenmatrix $\Sigma_g$; projecting g onto $\Sigma_g$; defining the establishment of coefficients as $c_g = \Sigma_g^+(g_i - \mu_g)$, where $\Sigma_g^+$ is the pseudo inverse of $\Sigma_g$, $\mu_g$ are extracted coefficients from a mean vector $\mu$ of linear model $\Sigma$; and defining the high resolution MCG image vector h as $h = \Sigma \cdot c_g + \mu$ The above objects also are met in a method of creating a magnetocardiogram (MCG) image from a sparse measurement output provided by a sensor unit including a plurality of electromagnetic sensors, each electromagnetic sensor contributing its output data to said sparse measurement output, said method comprising; defining high resolution to mean a resolution substantially higher than the resolution provided by said sparse measurement output; creating a plurality of synthesized high resolution magnetocardiogram images based on simulated electrical impulses within a three-dimensional spatial heart volume, as it would be perceived in an expected magnetocardiogram system; creating a linear model of the synthesized high resolution magnetocardiogram images to establish interpolation patterns between characteristics of the linear model and any sparse measurement output; and creating a representative high resolution MCG image by projecting said sparse measurement output onto the subspace of the linear model, and establishing coefficients.

Preferably in this method, the plurality of synthesized high resolution magnetocardiogram images includes more than one thousands images simulating perceived electrical impulses at different depths within said heart volume.

Further preferably, the synthesized high resolution MCG images are synthesized using the Biot-Savart Law.

If desired, the synthesized high resolution MCG images may be randomly generated.

In a preferred embodiment, the linear model is created using by principal component analysis (PCA).

Also in a preferred embodiment, the interpolation patterns are established by the following steps: (A) defining the following notation: N×N dense Bz magnetic field map to form a vector; M×M sparse measurement to form a vector; K randomly generated single current dipoles Q; (B) for each randomly generated current Q, compute N×N magnetic field map using Biot-Savart equation and stack the image to a vector $f_1$; (C) repeating step (B) to obtain K samples and get a data matrix $A=[f_1, f_2, \ldots f_K]$; and (D) train a PCA model given input data A, to obtain the eigenmatrix $\Sigma_f$.

In this approach, the representative high resolution MCG image is created by: given a new dipole and M×M sparse measurements $g_j$, finding the corresponding rows in the eigenmatrix, and denoting a resultant submatrix as $\Sigma_g$; projecting the sparse measurement to the PCA subspace and computing the coefficients as $c_g = \Sigma_g^+(g_j - g_{mean})$, where $\Sigma_g^+$ is an estimation of the inverse of $\Sigma_g$; and using the computed coefficients and original PCA space to reconstruct the dense magnetic field map Bz, as $f_j = \Sigma_j c_g + f_{mean}$.

More specifically, the step of creating a representative high resolution MCG image includes: defining the sparse measurement output as a vector g; defining the linear model as $\Sigma$; extracting from $\Sigma$ the row corresponding to sparse measurement output to form a sub-eigenmatrix $\Sigma_g$; projecting g onto $\Sigma_g$; defining the establishment of coefficients as $c_g = \Sigma_g^+ (g_i - \mu_g)$, where $E_g^+$ is the pseudo inverse of $\Sigma_g$, $\mu_g$ are extracted coefficients from a mean vector $\mu$ of linear model $\Sigma$; and defining the high resolution MCG image vector h as $h = \Sigma \cdot c_g + \mu$.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIGS. 12a to 12c show various equations useful in explanation of the present invention.

FIGS. 13a to 13d show various tables showing test results.

DESCRIPTION OF THE PREFERRED EMBODIMENTS

The presently preferred embodiment considers the high-res MCG image restoration as an example based super-resolution problem. Typically, one would require a library of true examples from which to learn characteristics of such true examples. However, since it is impractical to measure dense magnetic fields, and thus not feasible to obtain such true examples from direct measures, the presently preferred embodiment uses a model learning algorithm based on synthetic high-res MCG images.

The sample images are preferably randomly generated based on the Biot-Savart Law. From these sample images, a linear model is constructed a by use of principal component analysis (PCA). Sparse measurements from an MCG sensor unit are then projected into the subspace of the linear model to estimate model coefficients and restore a high-res MCG image as a model instance.

With a high-res MCG image thus reconstructed, it can then be analyzed to identify the location, depth, magnitude and orientation of an electric current.

As is explained above, an MCG image typically provides low-res, 2D MCG maps that do not provide enough information for directly recovering specific information of electrical currents. However, once the high-res MCG image is reconstructed, the 2D position of the electric current can be localized as the maximal point of the tangential components of the high-res MCG image. To improve the 2D localization accuracy, a nonlinear optimization algorithm is developed to solve the inverse problem. At the same time, the depth, magnitude and orientation of the electric current are also recovered. More specifically, the preferred algorithm alternates two steps iteratively. The first step estimates the 3D current position, and the second step reconstructs its magnitude and orientation. The 2D current location estimated from the model based restoration is used as the initialization. The present method is efficient, accurate and reliable without the need of special assumptions. For the sake of simplicity, the presently preferred system/method is illustrated as applied to a single electric current case only. It is to be understood, however, that extension of the present system/method to multiple currents is straightforward.

The present embodiment utilizes various computing devices (or data processing devices) to learn (i.e. create) a linear model from a set of high-res MCG images generated by random electric currents. Sparse data (i.e. a low resolution image) received from an MCG sensor unit is then projected onto the linear model, and a high resolution image representation of the low resolution image is created there from. An example of this approach is illustrated in FIG. 2.

Figure 1A:
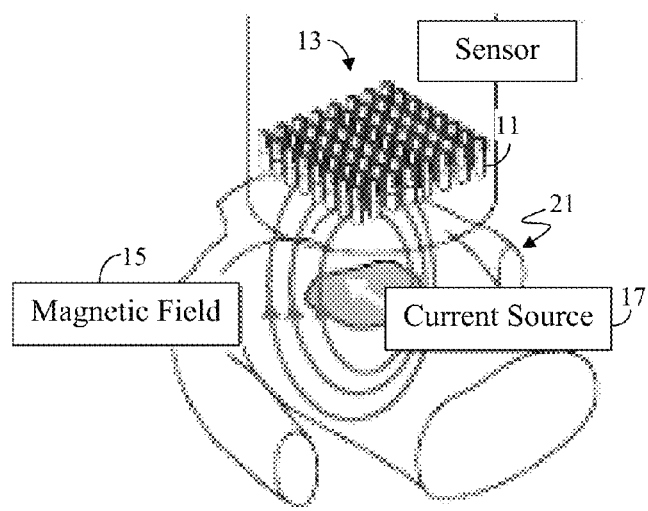
FIG. 1a illustrates an MCG measurement system in accord with the present invention.
Figure 2:
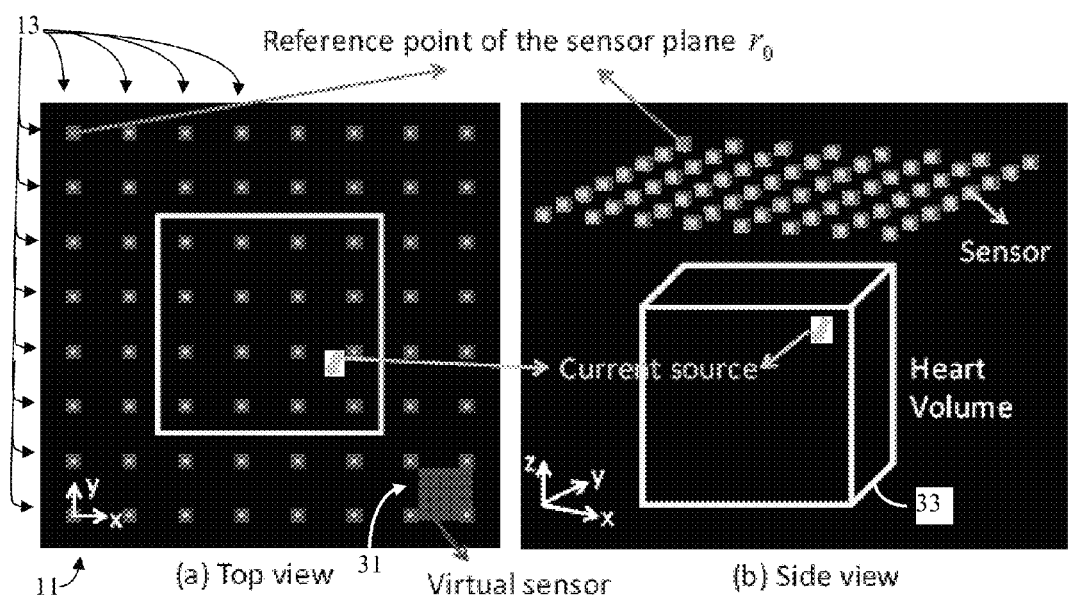
FIG. 2 illustrates a 2D sensor array in spatial relation with a heart volume in a simulation setup in accord with the present invention.

With reference to FIG. 2, the left-hand image (a) illustrates a top-view of a 2D sensor array (or sensor plane) in relationship with a side-view, 3D spatial heart volume 33 (right-hand image (b)) in a simulation setup. Left-hand image (a) is a top view of an MCG system, such as that shown in FIG. 1(a). In the present example, the top view (a) of FIG. 2 shows an MCG sensor unit 11 with 64 physical sensors 13 arranged in an 8×8 sensor array. In the present embodiment, however, four virtual sensors 31 are inserted between adjacent real, physical sensors 13, and the area within the square defined by physical sensors 13 and virtual sensors 31 is filled with a 4×4 array of additional virtual sensors 31. Thus, the present embodiment adds 1232 virtual sensors 31 to the 64 physical sensors 13 for a total of 1296 sensors. This is equivalent to a 36×36 sensor array, and constitutes the basis for the present high-res image. Assigning one image pixel per sensor, the present embodiment provides for a P×P (P >8) pixels in a high-res MCG image. Preferably, the sensor plane is 5 to 10 cm above the heart volume bounding box 33, which in the present case is 10×10×10 cm³. The electric current is represented by a vector located at a 3D point.

It is to be understood that the number of virtual sensors, and thus the value of P is design choice. A later experiment described below, for example, incorporates a higher number of virtual sensors to produce an even higher resolution MCG image.

FIGS. 12A to 12C show various equations (Eq. 1 to Eq. 12) to facilitate discussion of the present invention.

Given a single electric current, a magnetic field at each sensor 13 can be computed based on the Biot-Sarvart Law, equation Eq. 1, where $\vec{J}(\vec{p})$ is the moment of the current including its magnitude and orientation. In this case, $\vec{p}$ is the 3-dimensional (i.e. 3D) position vector of the current. Note that this representation of electric current is an approximation by assuming the size (or magnitude) of the current is zero. One can consider that the volume (size, or density) information is included in the moment vector $\vec{J}$. $\vec{B}(\vec{r}_m)$ is the magnetic vector measured by the $m_{th}$ sensor at position $\vec{r}_m = \vec{r}_o + \vec{\delta}_m$, where $r_o$ is the reference point of the sensor plane and $\delta m$ indicates the offset of the $m_{th}$ sensor with respect to $r_o$. As it is known in the art, $\mu_o$ is the magnetic constant.

In typical MCG systems, only the z component of $\vec{B}$ is measured.

From Eq. 1 one may compute $B_z$ (the z component of $\vec{B}$) by means of equation Eq. 2, where $J^1, J^2, J^3$ represent the three components of the current moment vector $\vec{J}$; $x_p, y_p, z_p$ represent the three components of the current position vector $\vec{p}$; and $r_m^1, r_m^2, r_m^3$ represent the three components of the sensor position vector $\vec{r}_m$.

In a training step, a set of high-res P×P MCG images (where P>>M) are generated. To generate each P×P MCG image, a single electric current with both random moment and 3D position is created. The high-res P×P MCG image is computed based on Eq. 2.

Figure 3:
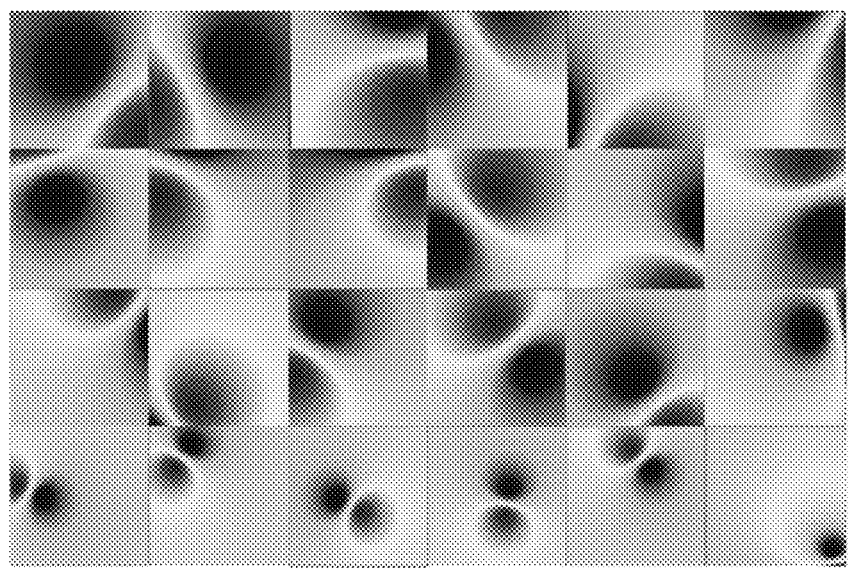
FIG. 3 shows various examples of training images in accord with the present invention.

Some examples of training images are shown in FIG. 3. Each high-res MCG image is generated by a single electric current with both random moment and 3D position. Since the magnetic field generated by the heart is very weak ($10^{-12}$ to $10^{-10}$ Tesla), the high-res MCG image is normalized to 0~255 and displayed using a JET color map. The images from different rows are generated from different depths (the distance of the electric current in z direction). In this manner, K high-res MCG training images are generated. All the image vectors (the mean vector is denoted by $\mu$) are centralized, and they are stacked into a matrix A. Matrix A thus consists of K columns of P×P vectors. PCA is applied to extract the eigenvectors of matrix A.

A received sparse M×M measurement from an MCG sensor unit defines a vector g. To restore (i.e. create) a high-res MCG image given a sparse M×M measurement (vector g), one first extracts the corresponding rows from the eigenmatrix $\Sigma$ to form a sub-eigenmatrix $\Sigma g$. Similarly, vector g's corresponding elements from mean vector $\mu$ form a sub-mean vector $\mu_g$. Vector g is then projected to sub-eigenmatrix $\Sigma g$, and model coefficients $c_g$ are calculated as $c_g = \Sigma_g^+(g_j - \rho_g)$, where $\Sigma_g^+$ is the pseudo inverse of $\Sigma g$. Finally the original eigenmatrix $\Sigma$ along with estimated coefficients $c_g$ are used to reconstruct the high-res MCG image vector h, as $h = \Sigma \cdot c_g + \mu$, where h is a P×P vector.

FIG. 3 illustrates four rows of different MCG images. The four rows of MCG images are generated at four respective depths, or layers, (i.e. different distances to electric current locations, or sources, in the z direction). A big variance can be seen between the MCG images when changing depths.

Figure 4A:
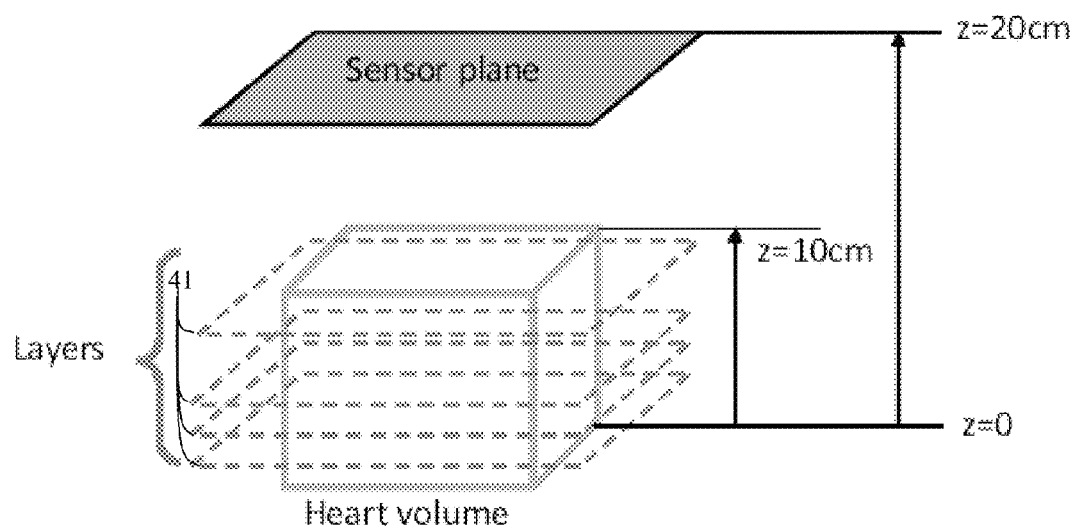
FIG. 4a illustrates the random generation of electric currents at different depth layers.

An illustration of these depth layers 41 is shown in FIG. 4A. In the presently preferred embodiment, electric currents are randomly generated at different depth layers 41. It would be too exhaustive to sample every depth to select a set of depth layers. This approach assumes that $B_z$ can be approximated as a linear function of the current depth, as is explained more fully below.

In the present approach, the sensor positions $\vec{r}_m$, the 2D position $(x_p, y_p)$, and the moment J of the electric current are fixed. $B_z$ is only affected by the depth z of the current. Thus, Eq. 2 can be simplified to Eq. 3, where $a_m$ and $b_m$ are constants but unknowns, c=20 cm is the depth of the sensor, and z is the depth of the current, which varies between 0 to 10 cm within the heart volume bounding box. Preferably, $a_m$ lies in a range from −7.5 to 7.5 cm, and $b_m$ lies in a range from 0 to 112.5 cm.

By applying Taylor expansion to Eq. 3, one obtains Eq. 4. By ignoring $O(\Delta z^3)$, one only needs to prove that $$\frac{d^2}{2dz} B_z^m(z)$$

is close to zero for any possible z and any sensor.

Figure 4B:
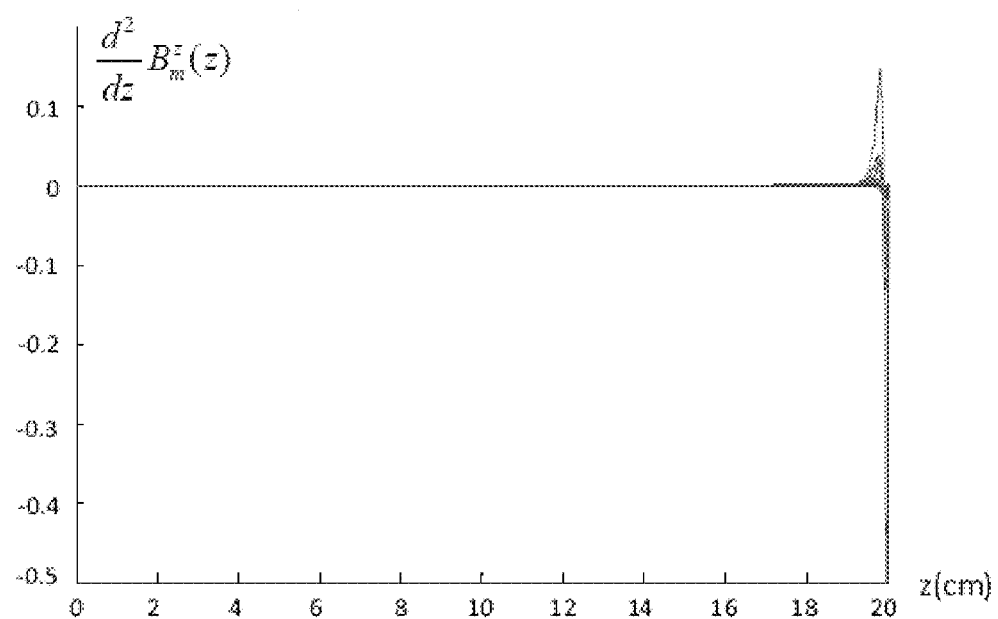
FIG. 4b plots the results of 64 trials at different depths, z.

A graph of $$\frac{d^2}{2dz} B_z^m(z)$$

versus depth, z, is shown in FIG. 4b. More specifically, the graph shows $$\frac{d^2}{2dz} B_z^m(z)$$

in 64 trials with random $a_m$ and $b_m$ in each trial. As shown, $$\frac{d^2}{2dz} B_z^m(z)$$

demonstrates a very small value (close to zero) when z varies from 0 to 10 cm. Therefore, a set of depth layers was sampled within this depth range, as is illustrated in FIG. 4a.

In the present experiments, 1000 samples were generated in each of 10 evenly distributed depth layers. The presently preferred method of creating a restored high-res MCG image was then compared with the bicubic interpolation method, as well as with the actual, ground truth images.

Figure 5:
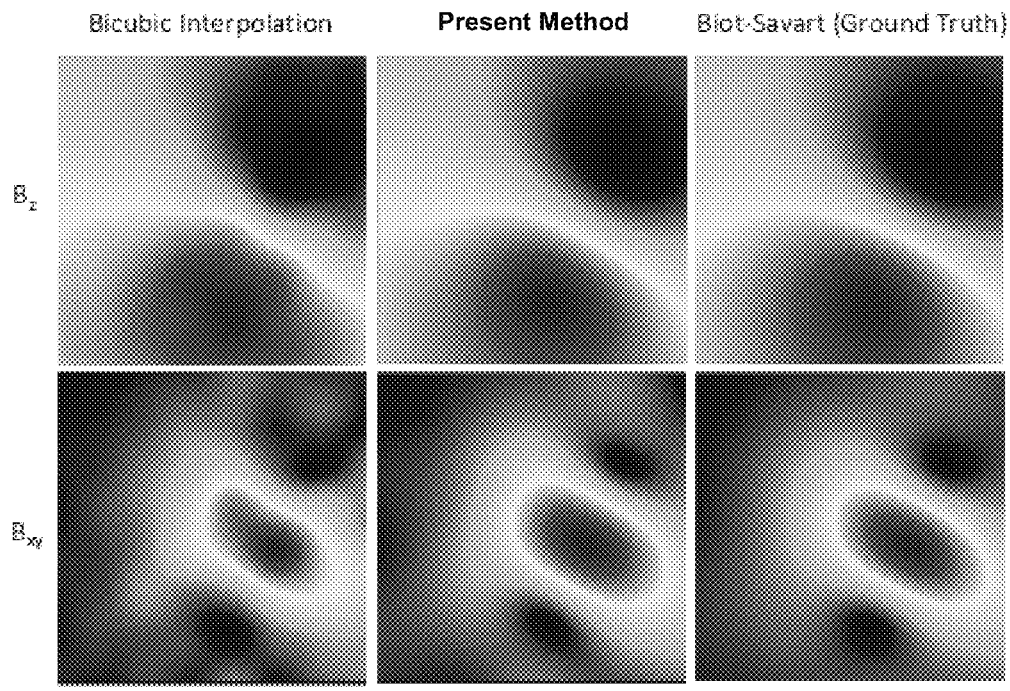
FIG. 5 compares high-res MCG images created using the present invention with a prior art method and with a ground truth example.

With reference to FIG. 5, a restored high-res MCG image generated by the bicubic interpolation is shown adjacent a corresponding high-res MCG image generated according to the present method. For evaluation purposes, a high-res MCG image reconstructed from the ground truth current based on the Biot-Sarvart Law is shown on the right. To better simulate physical conditions, 5% uniformly distributed random noise is added to each sensor. As is visually evident from the side-by-side comparison of the three images, the high-res MCG image constructed by the present method more closely matches the ground truth MCG image. Thus the present method achieves a higher level of accuracy in constructing high-res MCG images.

As is mentioned above, a 2D estimate of the electric current location can be obtained by analyzing the high-res MCG image. A presently preferred method for improving the localization accuracy is to solve a nonlinear optimization that reconstructs both 3D position and moment of the electric current, i.e. the inverse problem. An accurate high-res MCG image restored by the linear model provides a good initialization for the inverse problem and helps it converge on the global optimum more quickly. The preferred method for generating a 2D estimate from a high-res MCG image is as follows.

Given a high-res MCG image $B_z(i,j)(i=1, 2, \ldots, N; j=1, 2, \ldots, N)$, the maximal point of the tangential components $B'_{xy}(i,j)$ of $B_z(i,j)$ refers to the 2D position $(x_p, y_p)$ of the electric current. This may be seen in the second row images of FIG. 5. The tangential components of $B_z(i,j)$ may be computed using equation Eq. 5. One now is left with solving the inverse problem.

Figure 6:
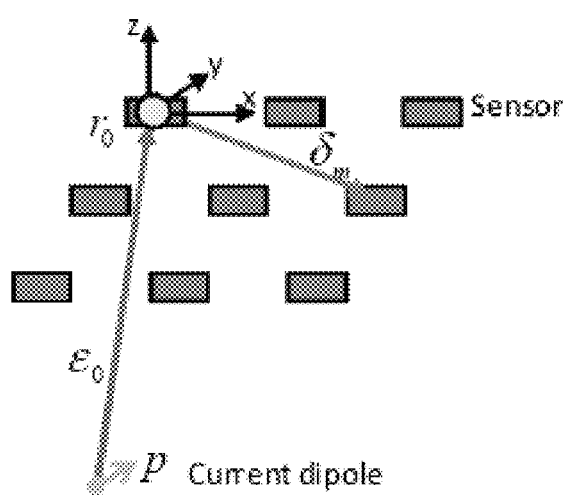
FIG. 6 illustrates the spatial configuration of sensors and electric current in accord with the present invention.

The inverse problem is to solve both 3D position $\vec{p}$ and moment $\vec{j}$ of the electric current. This approach may be better understood with reference to FIG. 6, where $\vec{r}_o$ is set as the world origin. If $\vec{p}$ is given, the inverse problem becomes a linear one. First, Eq. 1 may be rewritten as Eq. 6, where $\vec{B}^m = \vec{B}(\vec{r}_m)$, $\vec{J} = \vec{J}(\vec{p})$, and $$\vec{R}_m = \frac{\mu_o}{4\pi} \frac{(\vec{r}_m - \vec{p})}{\|\vec{r}_m - \vec{p}\|^3}.$$

Eq. 6 is then expanded to a matrix form by using a skew symmetric matrix, which results in Eq. 7. In this case, the z component of the magnetic field can be computed as shown in Eq. 8, where $R_m^1, R_m^2$ are x,y components of $\vec{R}$. Given M sensors, a linear system is defined as illustrated in equation Eq. 9, where B is a measured M×1 vector, R is a M×2 position matrix that is computed from given $\vec{p}$ and $\vec{\delta}_m$. In the present case, J is a 2×1 unknown vector. When rank(R)≥2 (this holds for the single electric current case with 64 sensors), one can solve a least square solution for J, as illustrated in equation Eq. 10.

Note that by only measuring $B_Z$ it is impossible to recover $J^3$. In fact, the magnetic field generated by the z component of the current only propagates along the horizontal direction and never reaches outside of the body. For the following computation, one sets $J^3=0$. Given an estimated current moment $\vec{J}=[J,0]$, one can update the current position $\vec{p}$.

Eq. 1 is rewritten as equation Eq. 11. One may then let $\alpha = 4\pi/\mu_0$ and $\vec{\epsilon}_0 = \vec{r}_0 - \vec{p}$. $\vec{\delta}_m$ is known for each sensor. One may then apply equation Eq. 12 to obtain $\alpha\vec{B}^m$. In Eq. 12, let $\vec{\tau}_m = \vec{J} \times \vec{\delta}_m$ and $\vec{\epsilon}_0 = (x_\epsilon, y_\epsilon, z_\epsilon)^T$. It is noted that $\vec{\tau}_m$ can be computed given $\vec{J}$. Again, the cross product is removed from Eq. 12 by using a skew-symmetric matrix. Therefore for each sensor m=1:M, one obtains a nonlinear equation in terms of $(x_\epsilon, y_\epsilon, z_\epsilon)$, as illustrated in Eq. 13. Letting $F=(f^1; f^2; \ldots; f^m)=0$, one then solves a least square solution of the nonlinear system F for $\vec{\epsilon}_0$.

Once the offset $\vec{\epsilon}_0$ is obtained, the position matrix R can be updated and J can be recomputed. These iterations are repeated until the algorithm converges. The inverse problem step converges in real time (0.5 seconds on average). Finally $\vec{p} = \vec{r}_0 - \vec{\epsilon}_0$. Since the high-res MCG image only provides an estimate for 2D current position $(x_p, y_p)$, the initial depth z and magnitude $\|\vec{J}\|$ of the electric current are given by equation Eq. 14, where d is the distance between two magnetic poles in the high-res MCG image.

The present high-res MCG image restoration method and electric current localization algorithm was evaluated using both simulations and physical phantom setups. In both scenarios the ground truth of the 3D position $\vec{p}_g$ and moment $\vec{J}_g$ of the electric current are known.

Figure 1B:
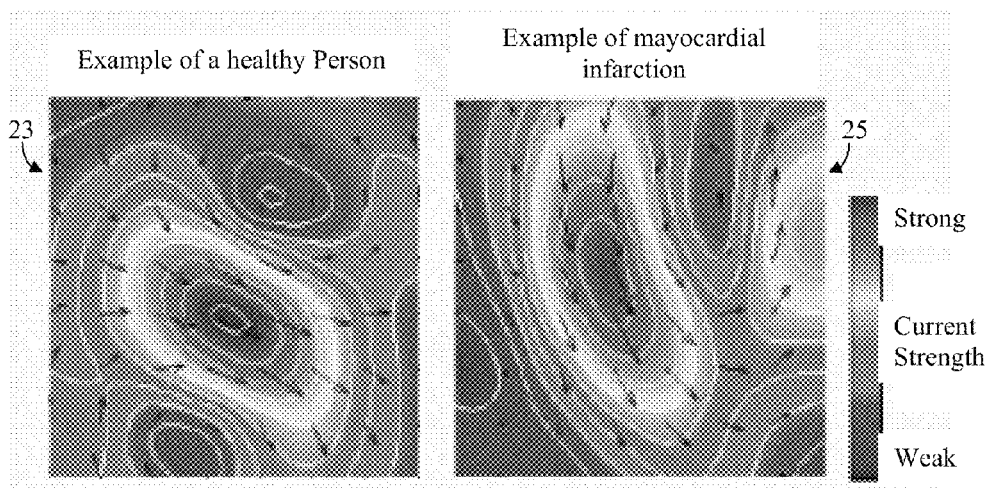
FIG. 1b compares the tangential image of a restored high-res MCG image of a healthy heart with that of an unhealthy heart.

The present simulation setup is similar to the setup showed in FIG. 1. There are 8×8 physical sensors 13 with a 2.5 cm sensor interval. The entire measuring area is 17.5×17.5 cm². The heart volume 19 is 10×10×10 cm³. The distance from the sensor array (or sensor unit) 11 to the top of the heart volume 19 is 5 cm. In each trial, a random electric current within the heart volume is generated. $B_z$ is computed at the 64 sensors 13, and 5%, 10% or 15% random noise is added to each sensor. This added noise has a uniform or Gaussian distribution. The 64 sparse measurements with noise are used to restore a high-res MCG image having an N×N resolution. To achieve this, 50 pixels are inserted between two adjacent real sensors, which means that the interval between adjacent pixels in the high-res MCG image is 0.5 mm. In this case N=50×7+1=351.

Tables 1 to 4 in FIGS. 13a to 13d, respectively, illustrate some simulation results. Table 1 in FIG. 13a shows the 2D electric current localization error with respect to different noise types and ratios over 200 trials (depth is not considered in this case). There are a number of previous works that report accuracy about the 2D electric current localization. For example, "Biomagnetic Noninvasive Localization of Accessory Pathways in Wolff-Parkinson-White Syndrome", in *Pacing and Clinical Electrophysiology*, by Weismuller et al., 14(111):1961-1965, 1991, and in "Magnetocardiographic Non-invasive Localization of Accessory Pathways in the Wolff-Parkinson-White Syndrome by a Multichannel System", in *European Heart J.*, by P. Weismuller and et al, 13(5):616-622, 1992, the 2D localization accuracy for Wolff-Parkinson-White (WPW) syndrome is between 0 cm to 5 cm, and average 1.8 cm. Also, "Magnetocardiographic Localization of Arrhythmia Substrates: a Methodology Study with Accessory Pathway Ablation as Reference", in *IEEE Trans. on Medical Imaging*, by P. L. Agren and et al., 17(3):479-485, 1998, reports the 2D localization accuracy for arrhythmia substrate as being 2.1 cm and 9.6 cm. Lastly, "Noninvasive Diagnosis of Arrhythmic Foci by Using Magnetocardiograms,—Method and Accuracy of Magneto-Anatomical Mapping System", in *J. of Arrhythmia*, by S. Yamada and et al., 16:580-586, 2000, and "Magnetocardiograms in clinical medicine: unique information on cardiac ischemia", by S. Yamada et al., in *Arrhythmias and Fetal Diagnosis*, 2005, show a similar setup consisting of 8×8 sensors, a 2.5 cm sensor interval, and a 5% random noise, but neither the sensor depth nor the noise type is reported. They report the 2D localization accuracy as being 1.4 mm+/−0.7 mm for simulation, 8 mm for WPW and 7 mm PCV. Compared to previous work, the method shows better accuracy than the current state of art.

Moreover, since the present method solves the inverse problem, the present method permits the reconstruction of the 3D position of the electric current and its moment. Applicants believe that the the present ability to reconstruct a 3D current is new to the present field.

Table 2 in FIG. 13b shows the 3D current localization error. When the noise level is increased, the depth reconstruction becomes less accurate, which can be caused by an inaccurate initialization. Table 4 in FIG. 13d shows the orientation difference between the reconstructed current moment $\vec{J}_{rec}$ and the ground truth current moment $\vec{J}_g$. As can be seen, the orientation of the electric current is very robust to not only the measurement noise, but also the depth error.

Figure 7:
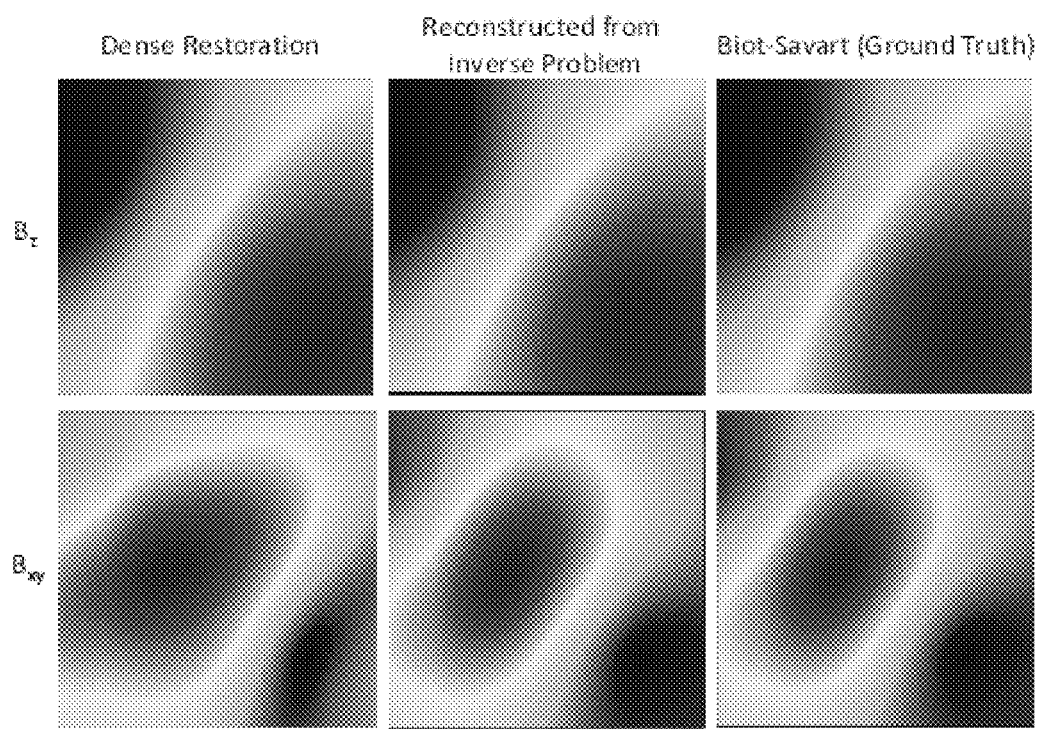
FIG. 7 compares high-res MCG images created using the present invention with a prior art method and with a ground truth example.

Table 3 in FIG. 13c shows the current magnitude reconstruction error. Since the current magnitude is very weak, the relative error is computed. All the results are averaged from 200 trials. FIG. 7 shows an example of a high-res MCG image restored by the linear model (left), a high-res MCG image computed given the reconstructed current ($\vec{J}_{rec}, \vec{p}_{rec}$) (middle), and a high-res MCG image computed given the ground truth current ($\vec{J}_g, \vec{p}_g$) (right), and 5% uniformly distributed random noise is added to each sensor.

Figure 8:
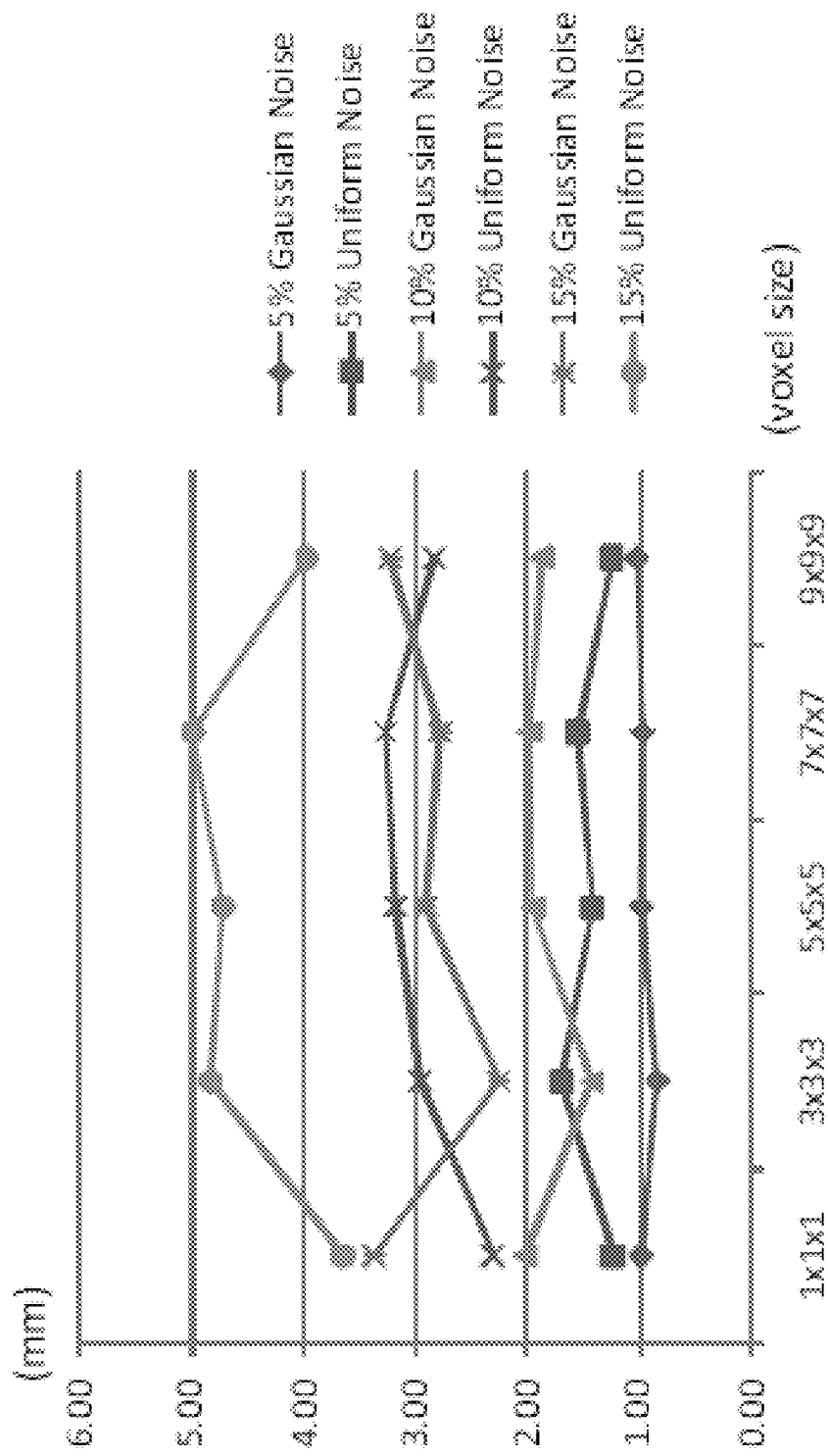
FIG. 8 illustrates 2D voxel current localization errors with respect to different sizes of voxel current.

In reality, an electric current is more like a voxel rather than a point. Different sizes of voxel currents were simulated by generating a set of point currents within a small cube by a 0.5 mm interval. FIG. 8 shows the 2D localization error for voxel currents. The geometric center of the voxel current is used as the ground truth. The results demonstrate that the present localization algorithm is robust to the size of the electric current, and comparable to the state of art (which only considers the point current).

Figure 9:
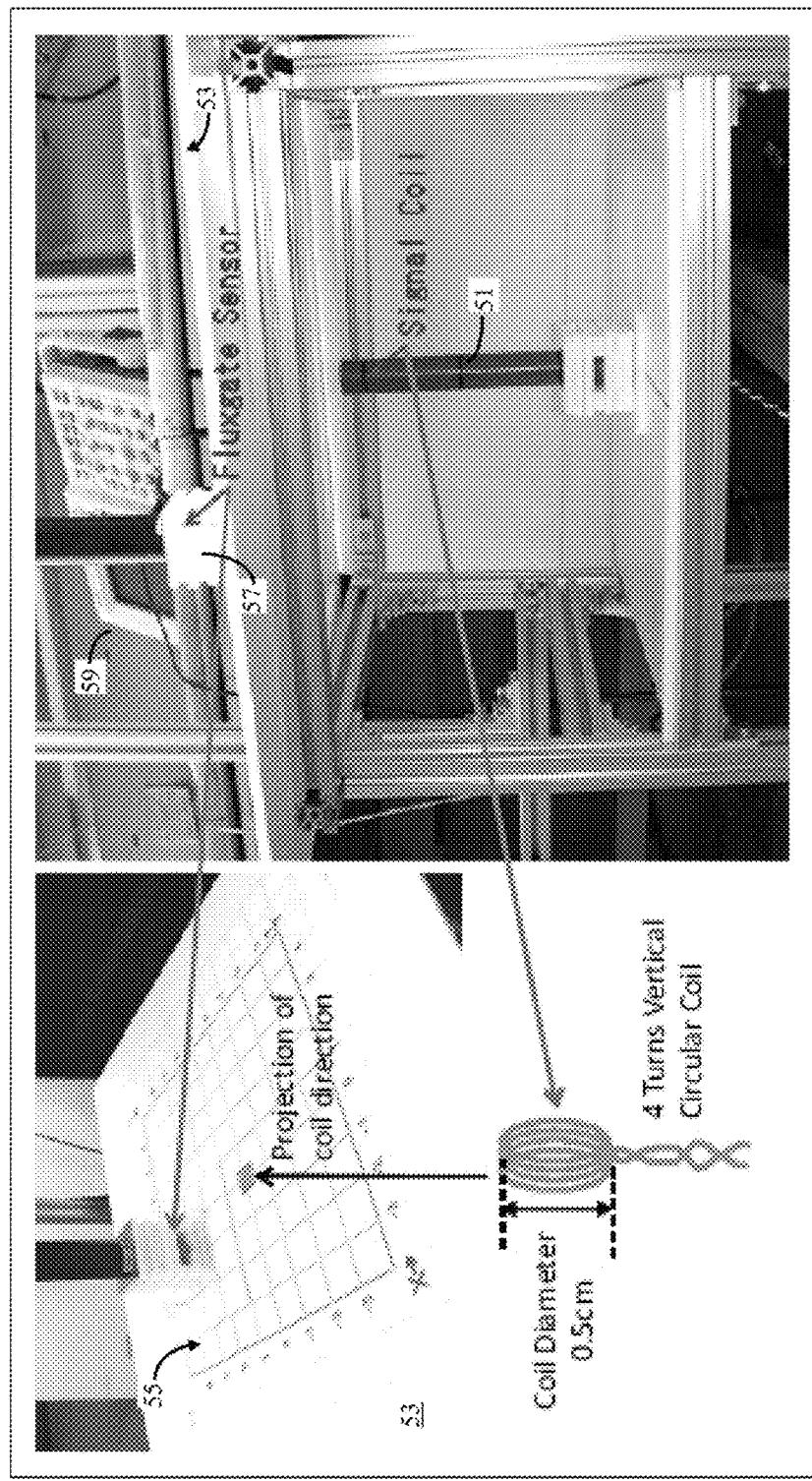
FIG. 9 shows a real phantom experimental setup in accord with the present invention.

A real phantom experiment is shown in FIG. 9. In this setup, a 4-turn vertical circular coil 51 is used as the ground truth current. It is built in a "Signal Coil" component. Above the coil there is a table 53 with a fixed (x,y) position but a varying z position with respect to the coil 51. On the table is printed an 8×8 grid 55 marked in 2 cm intervals, spanning from −4 to 3 in each direction. The coil 51 is right below the (0,0) coordinate. A fluxgate sensor 57 (Mag639™) is used to measure the z component of the magnetic field at each grid point. A spectrum analyzer 59 is used to read the signal from the fluxgate sensor.

In this real phantom experiment, the electric current has a physical shape and size. It can be considered as a set of small line segment currents. The present localization algorithm estimates the 2D position of the geometric center of the coil. By synchronizing the fluxgate sensor measurement with the AC generator, one can simulate an 8×8 MCG system. The output of the fluxgate sensor 57 is imported to the spectrum analyzer 59 and converted to measurements in Tesla.

Figure 10:
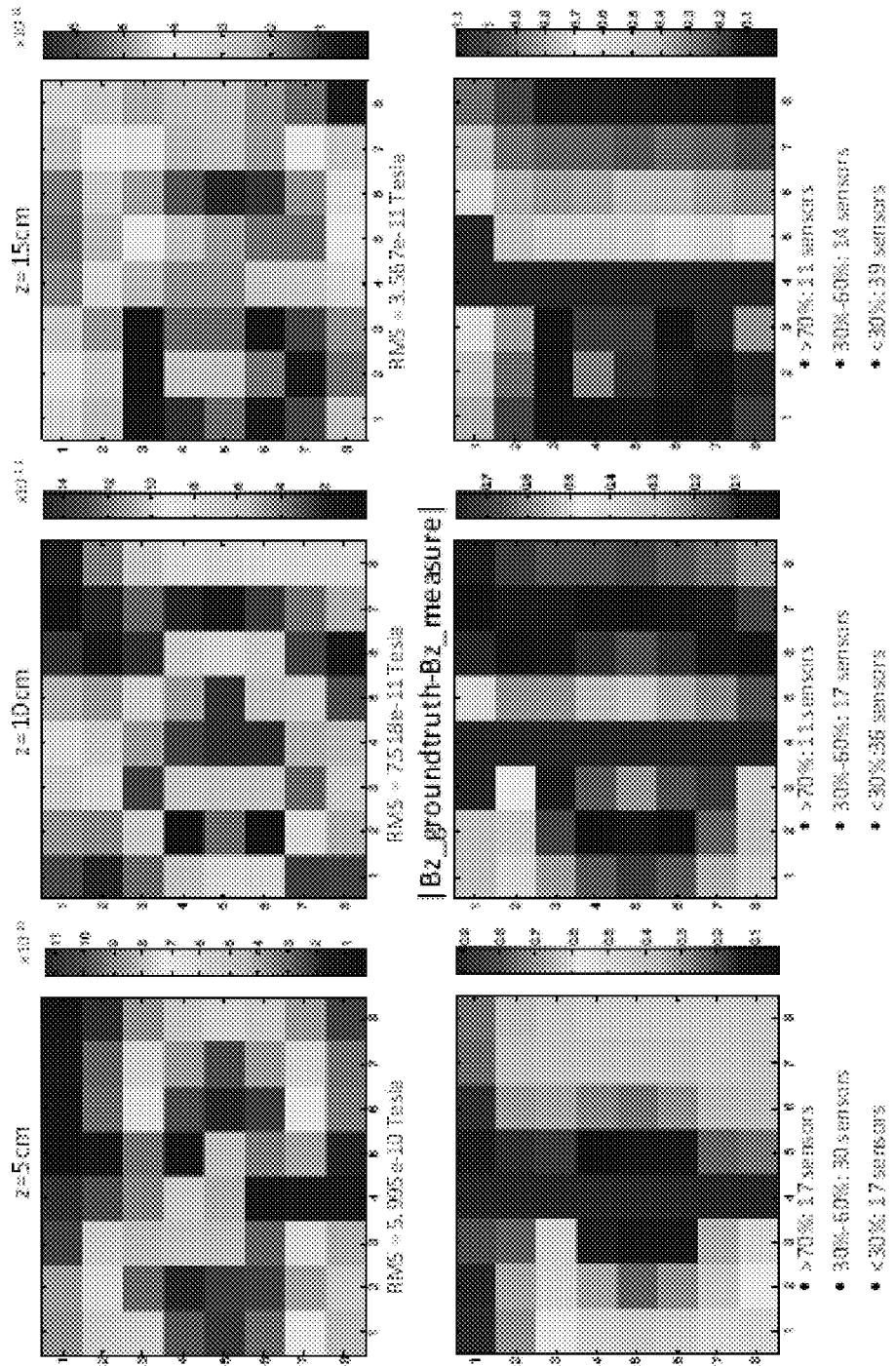
FIG. 10 illustrates the absolute and relative errors between the real measurement and the ground truth which is computed based on the Biot-Savart Law.
Figure 11:
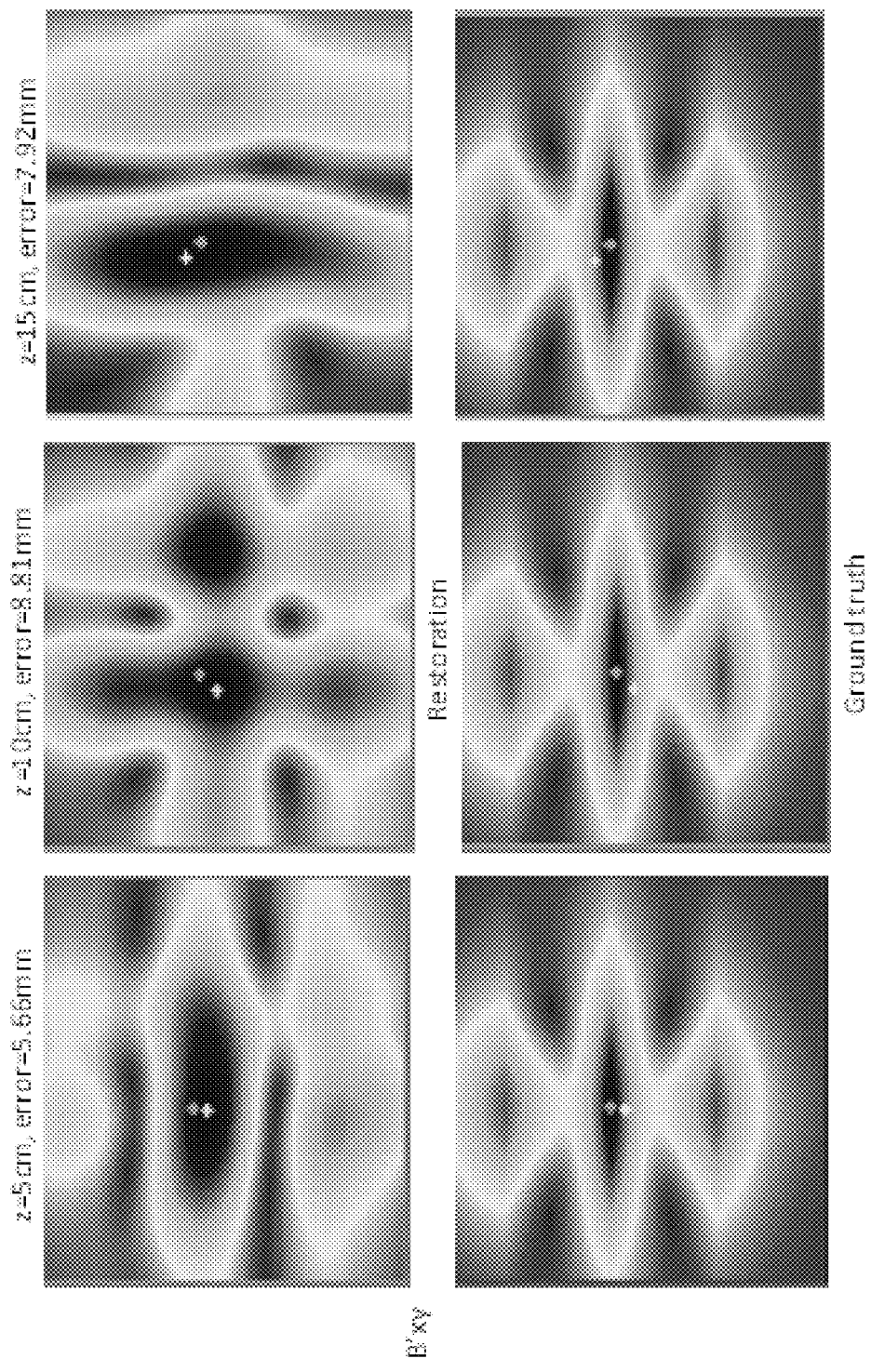
FIG. 11 shows 2D Localization results shown in $B'_{xy}(i,j)$ for three measurements while changing the distance between the sensor and the coil to: 5 cm, 10 cm and 15 cm.

The real phantom setup is totally unshielded thus the measurement noise is big, which is shown in FIG. 10. Three MCG measurements were simulated by changing the distance between the sensor and the coil to: 5 cm, 10 cm and 15 cm, and then estimated the 2D geometric center of the coil. FIG. 10 compares the absolute and relative errors between the real measurements and the ground truth measurements which are computed based on the Biot-Sarvart Law. When z=5 cm, over a ¼ of sensor measurements have over 70% noise; for other two cases the noise ratio is a little bit smaller but still about half of sensors have over 30% noise. Even in such a noisy setup, the present localization method can still achieve 6:9 mm 2D accuracy, as is shown in FIG. 11. When the sensor depth increases, high-res MCG images $B_z(i,j)$ and corresponding tangential components $B'_{x,y}(i,j)$ change much. However the global minimal point of $B'_{x,y}(i,j)$ stays close to the ground truth robustly. This is a very encouraging result compared to the state of art using shield MCG systems. It is noted that the best accuracy is achieved when z=5 cm although the measurement error is the biggest. One reason is that the local measurements closer to the coil are more accurate than the other two cases.

A couple of parameters can affect the accuracy of the high-res MCG image restoration and current localization.

Presently, the resolution is decreased by changing N from 351 to 141, i.e. 20 instead of 50 pixels are inserted between adjacent real (or physical) sensors, and the localization error is increased by 150%. On the other hand, when one inserts more than 50 pixels, the accuracy does not change much. The sensor number also affects the accuracy. With the same covering area (17.5×17.5 cm²), the more sensors that are used in the MCG system, the better the accuracy of the present algorithm that one can achieve. For example, with the 5% white Gaussian random noise, the localization error is 0.878 mm for 8×8 sensors; 0.850 mm for 10×10 sensors; 0.837 mm for 12×12 sensors; 0.768 mm for 18×18 sensors; and 0.660 mm for 36×36 sensors. These two parameters are therefore very important for MCG system design.

Hereinabove, only the single electric current localization problem is considered, and a good initialization can be computed from the dense MCG image. In reality there can be more than one electric voxel current. Signal decomposition might be needed for initialization of the multiple current localization. In summary the present method is capable of restoring/creating accurate high-res MCG images. The high-res MCG images are created in an efficient, accurate and reliable manner for single current 2D localization. In addition the present algorithm can reconstruct the depth and moment of the current. It can also be easily extended to solve for multiple current sources.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A magnetocardiogram (MCG) system comprising:
a sensor unit including M×M electromagnetic sensors producing an M×M measurement output of M×M data units, said M×M measurement output constituting a first MCG image;
a data processing device having a linear model defining a second MCG image of substantially higher resolution than said first MCG image, said second MCG image having a P×P resolution where P>M, said linear model establishing interpolation patterns between characteristics of the linear model and any data point of said M×M measurement output; and
a high resolution MCG image synthesizer producing a third MCG image by projecting said first MCG image onto the subspace of the linear model, and establishing coefficients for said third MCG image in accordance with the linear model and said M×M data units;
wherein the producing of said third MCG image includes:
defining the M×M measurement output as a vector g;
defining the linear model as $\Sigma$;
extracting from $\Sigma$ the row corresponding to the M×M measurement output to form a sub-eigenmatrix $\Sigma_g$;
projecting g onto $\Sigma_g$;
defining the establishment of coefficients as $c_g = \Sigma_g^+(g_i - \mu_g)$, where $\Sigma_g^+$ is the pseudo inverse of $\Sigma_g$, $\mu_g$ are extracted coefficients from a mean vector $\mu$ of linear model $\Sigma$; and
defining the high resolution MCG image vector h as $h = \Sigma \cdot c_g + \mu$.

2. The MCG system of claim 1, wherein said third MCG image has a P×P resolution.

3. The MCG system of claim 1, further having an electric current localizer for determining a position and momentum of an electric current in accord with said third MCG image, said electric current localizer evaluating the electromagnetic output data from each electromagnetic sensor in an x-y orientation (Bxy) assuming single dipole, computing dense Bxy from dense Bz, finding the image maximum in said third MCG image, and using this determined position information as a starting point in an iterative process for identifying a three-dimensional position vector $\vec{p}$ and momentum vector $\vec{J}$ for said electric current.

4. The MCG system of claim 3, wherein the identifying a three-dimensional position vector $\vec{p}$ and momentum vector $\vec{J}$ for said electric current further includes:

Given said third MCG image $B_Z(i,j)$ (i=1, 2, ..., N; j=1, 2, ..., N), the maximal point of the tangential components $B'_{xy}(i,j)$ of $B_z(i,j)$ refers to the 2D position $(x_p, y_p)$ of the electric current, and the tangential components of $B_z(i,j)$ is computed as $$B_{xy}(i,j) = \sqrt{(\partial B_z(i,j)/\partial x)^2 + (\partial B_z(i,j)/\partial y)^2} \; ;$$

and said iterative process for identifying position vector $\vec{p}$ and momentum vector $\vec{J}$ for said electric current includes:

(a) defining the Biot-Sarvart Law as $\vec{B}^m = \vec{J} \times \vec{R}_m = -\vec{R}_m \times \vec{J}$, where $\vec{B}_m = \vec{B}(\vec{r}_m)$, $\vec{J} = \vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Sarvart Law to a matrix form by using a skew-symmetric matrix:

$$\vec{B}^m = [\vec{R}_m]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]'$$

where $R_m^1$, $R_m^2$ are x,y components of $\vec{R}_m$, and for said M×M electromagnetic sensors one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimation of J defined as $J=(R^TR)^{-1}R^TB$;

(c) defining the Biot-Sarvart Law as $$\vec{B}^m = \frac{\mu_o}{4\pi} \frac{\vec{J} \times ((\vec{r}_o + \vec{\delta}_m) - \vec{p})}{\|(\vec{r}_o + \vec{\delta}_m) - \vec{p}\|^3} = \frac{\mu_o}{4\pi} \frac{\vec{J} \times (\vec{\varepsilon}_o + \vec{\delta}_m)}{\|\vec{\varepsilon}_o + \vec{\delta}_m\|^3}$$

letting $\alpha = 4\pi/\mu_0$ and $\vec{\epsilon}_0 = \vec{r}_0 - \vec{p}$, identifying $\vec{\delta}_m$ as known for each sensor to redefining the Biot-Sarvart Law as $$\alpha \vec{B}^m = \frac{\vec{J} \times \vec{\varepsilon}_o + \vec{J} \times \vec{\delta}_m}{\|\vec{\varepsilon}_o + \vec{\delta}_m\|^3}$$

letting $\vec{\tau}_m = \vec{J} \times \vec{\delta}_m$ and $\vec{\epsilon}_0 = (x_\epsilon, y_\epsilon, z_\epsilon)^T$ and computing $\vec{\tau}_m$ from $\vec{J}$, for each sensor m=1:M, defining a nonlinear equation in terms of $(x_\epsilon, y_\epsilon, z_\epsilon)$ as $$\alpha B_z^m + \frac{-J_{x_\varepsilon}^2 + J_{y_\varepsilon}^1 + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F = (f^1; f^2; \ldots; f^M) = 0$, and solving a least square solution of the nonlinear system F for $\vec{\epsilon}_0$;

(d) using $\vec{\epsilon}_0$ from step (c) to update the position matrix R and recompute J as in step (b), and iteratively repeating steps (b) and (c) until converges is achieved; and (e) defining the $\vec{p} = \vec{r}_0 - \vec{\epsilon}_0$, and defining the initial depth z and magnitude $\|\vec{J}\|$ of the electric current as $$z = d/\sqrt{2} \cdot 3 \text{ cm}, \|\vec{J}\| = \frac{4\pi d^2 B_z^{max}}{0.385 \, \mu_0}$$

where d is the distance between two magnetic poles in the third MCG image.

5. The MCG system of claim 1, wherein said linear model is defined as creating a plurality of synthesized magnetocardiogram images having the same resolution as said second MCG image, said synthesized magnetocardiogram images being based on simulated electrical impulses within a three-dimensional spatial heart volume, as it would be perceived in an expected magnetocardiogram system.

6. The MCG system of claim 5, wherein said plurality of synthesized magnetocardiogram images includes at least one thousand synthesized images simulating perceived electrical impulses per predefined depth level within said heart volume.

7. The MCG system of claim 5, wherein said synthesized MCG images are synthesized using the Biot-Savart Law.

8. The MCG system of claim 5, wherein said synthesized MCG images are based on randomly generated currents within said heart volume.

9. The MCG system of claim 5, wherein said linear model is created by using principal component analysis (PCA).

10. A magnetocardiogram (MCG) system comprising:
a sensor unit including M×M electromagnetic sensors producing an M×M measurement output of M×M data units, said M×M measurement output constituting a first MCG image;
a data processing service having a linear model defining a second MCG image of substantially higher resolution than said first MCG image, said second MCG image having a P×P resolution where P>M said linear model establishing interpolation patterns between characteristics of the linear model and any data point of said M×M measurement output; and
a high resolution MCG image synthesizer producing a third MCG image by projecting said first MCG image onto the subspace of the linear model, and establishing coefficients for said third MCG image in accordance with the linear model and said M×M data units;
wherein said interpolation patterns are established by the following steps:
(A) defining the following notation:
N×N dense Bz magnetic field map to form a vector;
M×M measurement output forms a vector;
K randomly generated single current dipoles Q;
(B) for each randomly generated current Q, compute N×N magnetic field map using Biot-Savart equation and stack the image to a vector $f_1$;
(C) repeating step (B) to obtain K samples and get a data matrix $A=[f_1, f_2, \ldots f_K]$; and
(D) training a PCA model given input data A, to obtain the eigenmatrix $\Sigma_f$.

11. The MCG system of claim 10, wherein said third MCG image is created by:
given a new dipole and M×M measurement output $g_j$, finding the corresponding rows in the eigenmatrix, and denoting a resultant submatrix as $\Sigma_g$;
projecting the M×M measurement output to the PCA subspace and computing the coefficients as $c_g=\Sigma_g^+(g_j-g_{mean})$, where $\Sigma_g^+$ is an estimation of the inverse of $\Sigma_g$; and
using the computed coefficients and original PCA space to reconstruct the dense magnetic field map Bz, as $f_j=\Sigma_f c_g + f_{mean}$.

12. A method of creating a magnetocardiogram (MCG) image from a measurement output provided by a sensor unit including a plurality of electromagnetic sensors, each electromagnetic sensor contributing its output data to said measurement output, said method comprising:
providing a data processing device to implement the following steps:
defining high resolution to mean a resolution substantially higher than the resolution provided by said measurement output;
creating a plurality of synthesized high resolution magnetocardiogram images based on simulated electrical impulses within a three-dimensional spatial heart volume, as it would be perceived in an expected magnetocardiogram system;
creating a linear model of the synthesized high resolution magnetocardiogram images to establish interpolation patterns between characteristics of the linear model and any measurement output; and
creating a representative high resolution MCG image by projecting said measurement output onto the subspace of the linear model, and establishing coefficients;
wherein the step of creating a representative; high resolution MCG image includes:
defining the measurement output as a vector g;
defining the linear model as $\Sigma$;
extracting from $\Sigma$ the row corresponding to measurement output to form a sub-eigenmatrix $\Sigma_g$;
projecting g onto $\Sigma_g$;
defining the establishment of coefficients as $c_g=\Sigma_g^+(g_i-\mu_g)$, where $\Sigma_g^+$ is the pseudo inverse of $\Sigma_g$, $\mu_g$ are extracted coefficients from a mean vector $\mu$ of linear model $\Sigma$; and
defining the high resolution MCG image vector h as $h=\Sigma \cdot c_g + \mu$.

13. The method of claim 12, wherein said plurality of synthesized high resolution magnetocardiogram images includes more than one thousand image simulating perceived electrical impulses at different depths within said heart volume.

14. The method of claim 12, wherein said synthesized high resolution MCG images are synthesized using the Biot-Savart Law.

15. The method of claim 12, wherein said synthesized high resolution MCG images are based on randomly generated currents within said heart volume.

16. The method of claim 12, wherein said linear model is created using by principal component analysis (PCA).

17. The method of claim 12, wherein said interpolation patterns are established by the following steps:
(A) defining the following notation:
N×N dense Bz magnetic field map to form a vector;
M×M measurement to form a vector;
K randomly generated single current dipoles Q;
(B) for each randomly generated current Q, compute N×N magnetic field map using Biot-Savart equation and stack the image to a vector $f_1$;
(C) repeating step (B) to obtain K samples and get a data matrix $A=[f_1, f_2, \ldots f_K]$; and
(D) train a PCA model given input data A, to obtain the eigenmatrix $\Sigma_f$.

18. The method of claim 17, wherein said representative high resolution MCG image is created by:
given a new dipole and M×M measurements $g_j$, finding the corresponding rows in the eigenmatrix, and denoting a resultant submatrix as $\Sigma_g$;
projecting the measurement to the PCA subspace and computing the coefficients as $c_g=\Sigma_g^+(g_j-g_{mean})$, where $\Sigma_g^+$ is an estimation of the inverse of $\Sigma_g$; and
using the computed coefficients and original PCA space to reconstruct the dense magnetic field map Bz, as $f_j=\Sigma_f c_g + f_{mean}$.

* * * * *